(12) United States Patent
Mischak et al.

(10) Patent No.: US 7,258,775 B2
(45) Date of Patent: Aug. 21, 2007

(54) METHOD AND DEVICE FOR THE QUALITATIVE AND/OR QUANTITATIVE ANALYSIS OF A PROTEIN AND/OR PEPTIDE PATTERN OF A LIQUID SAMPLE THAT IS DERIVED FROM THE HUMAN OR ANIMAL BODY

(75) Inventors: Harald Mischak, Sehnde ot Müllingen (DE); Hermann Haller, Hannover (DE)

(73) Assignee: mosaiques diagnostics and therapeutics AG, Hannover (DE)

( * ) Notice: Subject to any disclaimer, the term of this patent is extended or adjusted under 35 U.S.C. 154(b) by 271 days.

(21) Appl. No.: 10/275,096

(22) PCT Filed: May 4, 2001

(86) PCT No.: PCT/DE01/01691

§ 371 (c)(1),
(2), (4) Date: Nov. 1, 2002

(87) PCT Pub. No.: WO01/84140

PCT Pub. Date: Nov. 8, 2001

(65) Prior Publication Data
US 2003/0132114 A1  Jul. 17, 2003

(30) Foreign Application Priority Data
May 4, 2000  (DE)  ................. 100 21 737

(51) Int. Cl.
*G01N 27/447*  (2006.01)
(52) U.S. Cl. ................. 204/452; 204/603; 250/288
(58) Field of Classification Search ................. 204/452, 204/603; 250/688, 288; 702/22, 27
See application file for complete search history.

(56) References Cited

U.S. PATENT DOCUMENTS

| 4,994,165 A | 2/1991 | Lee et al. |
|---|---|---|
| 6,103,537 A * | 8/2000 | Ullman et al. ............. 436/526 |
| 6,875,616 B1 | 4/2005 | Forssmann et al. |

FOREIGN PATENT DOCUMENTS

| DE | 44 15 480 | 11/1995 |
|---|---|---|
| WO | WO96/33410 | 10/1996 |
| WO | WO98/07036 | 2/1998 |
| WO | WO98/35226 | 8/1998 |
| WO | WO99/46047 | 9/1999 |
| WO | WO 01/84140 | 11/2001 |

OTHER PUBLICATIONS

Liu et al, J. Chromatography A, 855 (1999), pp. 695-707.*
Majors et al, Rapid Communications in Mass Spectrometry, 10, pp. 1421-1426, 1996.*

(Continued)

*Primary Examiner*—Kaj K. Olsen
(74) *Attorney, Agent, or Firm*—Collard & Roe, P.C.

(57) ABSTRACT

The invention relates to a method for the qualitative and/or quantitative analysis of a protein and/or peptide pattern of a liquid sample that is derived from the human or animal body. The proteins and peptides of the liquid sample are separated by capillary electrophoresis, then directly ionized and transferred for analysis online via an interface to a mass spectrometer coupled thereto.

16 Claims, 1 Drawing Sheet

OTHER PUBLICATIONS

Figure 1:
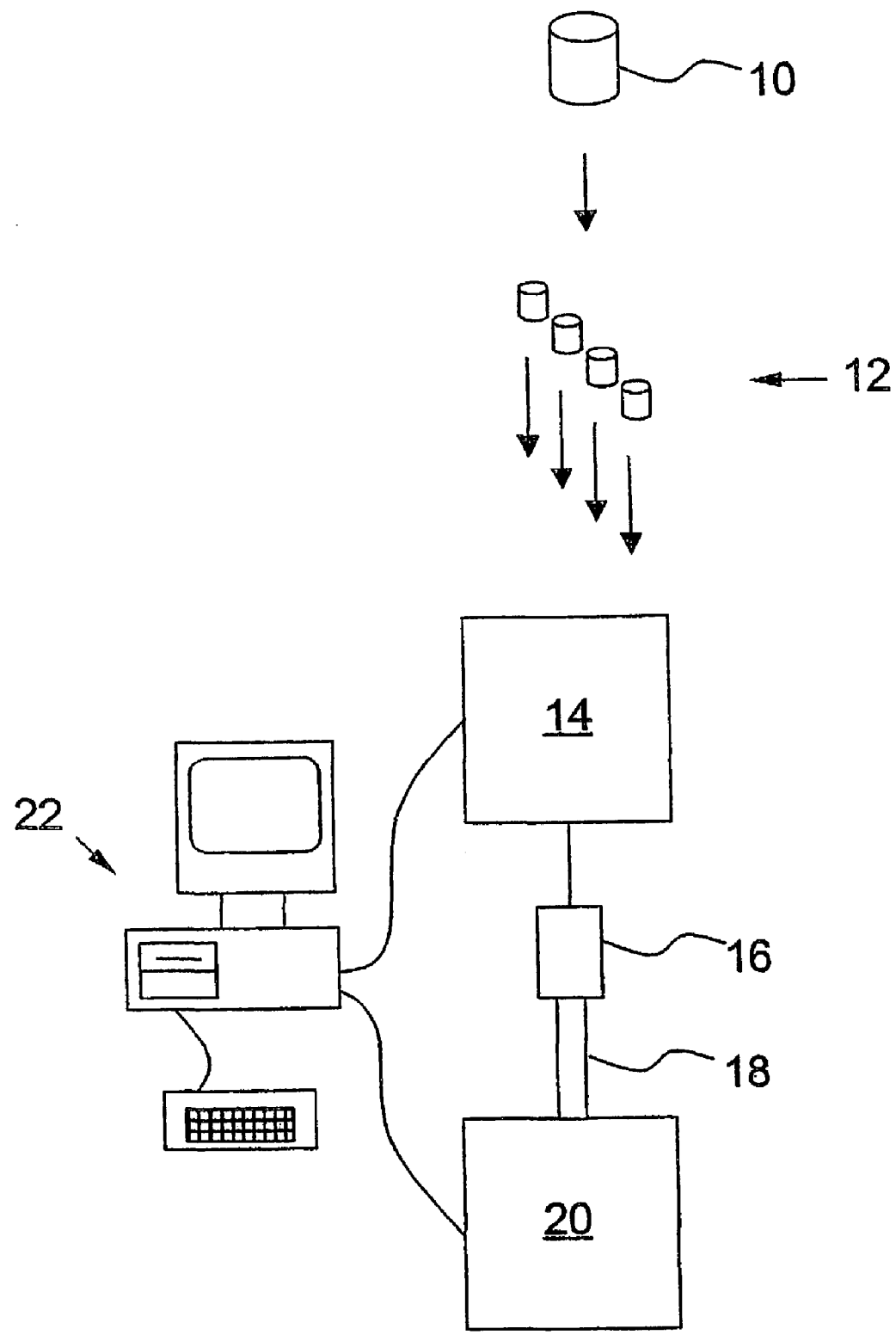

Haynes et al "Proteins of rat serum: I. Establishing a reference two-dimensional electrophoresis . . . ", Electrophoresis 19 (1998) pp. 1483-1492.*

Miller et al. "Proteins of rat serum: II. Influences of some biological . . . ", Electrophoresis 19 (1998) pp. 1493-1500.*

Fang et al. (Nov. 1994) "On-Line Time-of-Flight Mass Spectrometric Analysis of Peptides Separated by Capillary Electrophoresis", Anal. Chem. Bd. 66, Nr. 21, pp. 3696-3701.

Figeys et al. (Jun. 1996) "Protein Identification by Capillary Zone Electrophoresis/Microelectro Spray Ionization-Tandem Mass Spectrometry at the Subfemtomole Level", Anal. Chem. Bd. 68, pp. 1822-1828.

List of references filed in parallel European Patent, date not available.

LaBadie et al., "Low Molecular Weight Urinary Peptides in Ceroid-Lipofuscinoses: Potential Biochemical Markers for Juvenile Subtype" American Journal of Medical Genetics (1990) pp. 592-599.

Rohde E. et al. "Comparison of protein mixtures in aqueous humor by membrane preconcentration—capillary electrophoresis—mass spectrometry" Electrophoresis 1998, vol. 19, pp. 2361-2370.

Finnegan MAT, MAT 900 Mass Spectrometer System (1993).

Jarman et al., "An Algorithm for Automated Bacterial Identification Using Matrix-Assisted Laser Desorption/Ionization Mass Spectrometry", Anal. Chem. (2000), vol. 72, pp. 1217-1223.

* cited by examiner

METHOD AND DEVICE FOR THE QUALITATIVE AND/OR QUANTITATIVE ANALYSIS OF A PROTEIN AND/OR PEPTIDE PATTERN OF A LIQUID SAMPLE THAT IS DERIVED FROM THE HUMAN OR ANIMAL BODY

CROSS REFERENCE TO RELATED APPLICATIONS

Applicants claim priority under 35 U.S.C. §119 of German Application No. 100 21 737.0 filed May 4, 2000. Applicants also claim priority under 35 U.S.C. §365 of PCT/DE01/01691 filed May 4, 2001. The international application under PCT article 21(2) was not published in English.

The invention relates to a method of and a device for qualitative and/or quantitative determination of a protein and/or peptide pattern of or in a liquid sample which has been derived from a human or animal body for monitoring its condition. In accordance with the method, the peptides and proteins of the liquid sample are senarated by capillary electrophoresis. then are ionized directly and transferred online to a mass spectrometer connected to it for detection via an interface online. The device includes a capillary electrophoresis device, an ionization unit, a mass spectrometer connected via an interface online and a computer unit having a program for controlling the device as well as for automatic analysis and storage of the measured values and for comparing new measured values with the measured values already stored, The functions of the human and animal body are subject to a very complex and precise control. This is accomplished by means of proteins and peptides through the serum, among other things.

Cytokines play a decisive role here. These are polypeptides which are excreted by cells into the blood or the surrounding tissue and influence functions such as division, growth or propagation of other cells after binding to specific receptors. Cytokines regulate, among other things, the complicated interaction of the cells of the immune system.

The cytokines also include the so-called interleukins, which are mediator substances of the immune system, which are produced by leukocytes in low concentrations and have an influence on the growth, differentiation and activity of cells of the immune system.

To determine the functions and the condition of a human or animal body, qualitative and/or quantitative determination of the proteins and/or peptides of a liquid sample that is derived from a human or animal body is necessary.

Use of enzyme immunoassays is known for qualitative and/or quantitative determination of individual proteins or peptides in liquid samples derived from a human or animal body. In principle, an antigen-antibody reaction is linked to an enzyme reaction here, where either antibody-enzyme conjugates or antigen-enzyme conjugates are used, determining by measuring the enzyme activity of the conjugate after adding a suitable substrate.

In general, the solid-phase technique of ELISA (enzyme-linked immunosorbent assay) is used, where the antigen is bound to the solid phase either by direct adsorption or by another antibody.

Some proteins and peptides are determined quantitatively and/or qualitatively as part of medical clinical tests today.

A precise knowledge of the proteins and peptides and their concentration in liquid samples, in particular in the serum, is becoming increasingly important in medical clinical testing.

It has been found that the condition of a human or animal body can be described relatively well by using the protein and/or peptide pattern.

One disadvantage of the ELISA method as it has been practiced in the past, however, is that only one protein or peptide can be determined at one time. Therefore, to obtain the most complete possible protein and/or peptide pattern, a multitude of proteins and/or peptides must therefore be determined individually.

In addition, many proteins or peptides cannot be determined because no reagents, e.g., specific antibodies, which are necessary for detection are available.

Because of the small number of measurements, it is then difficult to draw relevant conclusions regarding the condition of a human or animal body.

In particular, the results of the medical clinical tests are not available until several hours after taking the liquid sample, so that prompt information regarding the condition of the human or animal body cannot be obtained.

Therefore, it is impossible with the ELISA method to derive a comprehensive and therefore relevant protein and peptide pattern.

Another disadvantage of the ELISA method is that comparative measurements of samples of various known protein or peptide concentrations, so-called standards, are necessary in order to determine the concentration of individual proteins or peptides in unknown liquid sample. These measurements are also time-consuming and cost-intensive, because only a single protein or peptide can be determined at one time.

International Patent WO 98 35 226 A describes a method of analyzing liquid samples whose components are separated by capillary electrophoresis, then ionized directly and transferred via an interface to a mass spectrometer connected to it for detection.

However, the known methods of analysis do not permit identification of similar or different conditions of the human or animal body.

The object of this invention is to provide a method of qualitative and/or quantitative determination of a protein and/or peptide pattern in a liquid sample derived from a human or animal body, and a device for implementing and analyzing the method for a complete and rapid determination of the proteins and/or peptides, and in addition, it makes it possible to identify similar or different conditions of the human or animal body.

This object is achieved by a method wherein to monitor the condition of a human or animal body for a longer period of time, reference values and sample values which describe conditions as well as deviations and correspondences derived therefrom are automatically stored in a database, and the best possible correspondence is automatically sought in the case of a new protein and/or peptide pattern determination, and a device wherein to monitor the condition of a human or animal body for a lonaer period of time, the program automatically stores reference values and sample values which describe conditions as well as the deviations and correspondences derived therefrom in a database, and it automatically searches for the best possibLe correspondence in the case of a new protein and/or peptide pattern determination. Refinements and advantageous embodiments are discussed below.

In the method according to this invention for qualitative and/or quantitative determination of a protein and/or peptide pattern in a liquid sample that is derived from a human or animal body, the proteins and/or peptides in the liquid sample are separated by capillary electrophoresis, then ionized directly and transferred online via an interface to a mass spectrometer connected thereto for detection; in order to monitor the condition of a human or animal body for a longer period of time, reference values and sample values describing conditions are automatically stored in a database and the best possible correspondences are automatically sought in a new protein and/or peptide pattern determination.

A reliable qualitative and/or quantitative determination of proteins and/or peptides in a complex matrix, such as that formed by human or animal body fluids, requires first the use of a method of separating substances. In this case, capillary electrophoresis has proven to be a suitable separation method.

The separation principle of electrophoresis is based on the different migration properties of electrically charged particles in solution when an electric field is applied. The advantage of the capillaries is the favorable ratio of surface to volume, which permits good removal of the Joulean heat generated by electric current flow. This in turn makes it possible to apply high voltages (usually up to 30 kV) and thus permits a high separation efficiency and short analysis times.

The high separation efficiency permits the determination of a complete protein and/or peptide pattern in a liquid sample. The short analysis times make it possible to obtain information quickly regarding the condition of the human or animal body, based on the liquid sample.

With the help of capillary electrophoresis, it is possible to separate neutral molecules, cations and anions. When an electric current is applied, neutral particles migrate at the rate of the electroosmotic flow, the cations being accelerated toward the cathode and the anodes being retarded.

For detection of the proteins separated by capillary electrophoresis, the capillary electrophoresis device is connected to a mass spectrometer.

Mass spectrometry makes it possible to determine the molecular weight of free ions in a high vacuum. It contains a mass analyzer, which separates the ions according to their mass/charge quotients (m/z), and a detector.

A suitable transition, a so-called interface, is provided, because ionization takes place under atmospheric pressure, but mass analysis requires a high vacuum.

With mass spectrometry, it is possible to routinely measure 10 fmol of a peptide and/or a small protein, i.e., 0.1 ng of a 10 kDa protein, with a measurement accuracy of ±0.01% from a complex mixture. Amounts of even less than 0.1 fmol have been measured experimentally.

This method is thus especially suitable for analyzing complex liquid samples that are derived from the human or animal body to detect the presence of certain proteins and peptides.

The resulting measured values are automatically analyzed and stored and new measured values are automatically compared with the measured values already stored.

Due to the comparison, corresponding and differing parameters are determined, and can then be used to describe the condition of a human or animal body.

By means of the database, it is possible to identify the same, similar or different conditions of the human or animal body.

In determinations of several liquid samples derived at intervals in time from the same human or animal body, the changes in the protein and/or peptide pattern are determined, analyzed and stored automatically.

This ensures the monitoring of the condition of a human or animal body over a longer period of time.

A database consisting of reference values, sample values, deviations and correspondences which describe certain conditions is automatically compiled, and there is an automatic search for the best possible correspondences in the case of new measurements. This makes it possible to have conditions of the human or animal body determined automatically.

It is provided in particular that serum or urine is used as the liquid sample.

These are liquid samples that are derived from the human body and having a protein and/or peptide composition which is especially suitable for obtaining information regarding the condition of the human or animal body.

Mass spectrometric analysis has the advantage over the conventional methods in use at the present time that the concentration of many peptides and proteins (>100) of a serum or urine sample can be determined by means of a single analysis. In addition, it is possible to identify as yet unknown proteins or peptides, which describe the condition of the human or animal body.

The method according to this invention achieves the result that in comparison with the traditional determination methods, only a single operation is necessary to determine several proteins and/or peptides. This saves both time and money.

The resulting mass spectrum may be used as a type of "fingerprint" to describe the overall condition of a human or animal body. In particular, it is also possible to analyze only certain regions of the mass spectrum.

Secondly, however, it is also possible to identify the proteins individually and to draw conclusions regarding the condition of the human or animal body on the basis of the presence, absence and concentration of these proteins.

In addition, it is also provided that the protein and peptide pattern, such as the pattern of cytokines, in particular the interleukins, is determined.

According to the information currently available, these proteins are essential proteins which regulate the functions of the human and animal body.

A refinement of this invention provides for the liquid sample to be acidified first before separating it by capillary electrophoresis, to purify it to remove unwanted particles by ultracentrifugation and/or to divide it by ultrafiltration into fractions containing proteins or peptides of a certain molecular size.

After acidifying, e.g., with formic acid to a pH of 3, it is possible to separate the unwanted insoluble constituents of the sample by ultracentrifugation. Fractionation of the liquid sample yields the result that, for example, only fractions of proteins and/or peptides of a certain molecular weight that are needed to describe the condition of the human or animal body are analyzed.

It is then provided that the fractions are composed of proteins and/or peptides of a molecular weight of <3 kDa, 3-30 kDa, 30-50 kDa and >50 kDa.

For example, if interleukins belonging to the group of cytokines, mainly including glycoproteins having a molecular weight of 17 kDa to 26 kDa, are to be determined, it is sufficient to use the fraction from proteins and/or peptides having a molecular weight of 3 to 30 kDa. This in turn means that analysis times can be shortened.

In addition, it is possible for the proteins and/or peptides to be detected immediately after they are separated but before they are ionized.

A number of methods are already known for detection of proteins and/or peptides separated by capillary electrophoresis, permitting good quantitative and qualitative analysis of samples, but only in exceptional cases.

Therefore, the proposed detection method is suitable for a more precise determination of proteins and/or peptides only in combination with mass spectrometry.

An advantageous embodiment of this invention provides for electrospray ionization to be used for ionization of the proteins and/or peptides.

To do so, the molecules in solution are sprayed under the influence of a high voltage (1-8 kV) among other things, at first forming small charged particles which become smaller due to evaporation of the solvent. Finally, free gaseous ions are formed.

Electrospray ionization is a mild ionization technique because of the relatively low levels of energy acting on the molecules, so that even sensitive molecules and to some extent even non-covalent aggregates enter the mass analyzer without decomposing.

It is advantageous that no molecular fragments are formed primarily in electrospray ionization. Although this may make it more difficult to elucidate the molecular structure, it does permit a very good identification of the proteins and/or peptides dissolved in the liquid sample.

The fragments nevertheless obtained in ionization may be used to advantage for identification of the amino acid sequence in the case of the smaller peptides, e.g., oligopeptides with less than 20 amino acids.

In addition, it is also possible to use a so-called time-of-flight (TOF) mass spectrometer as the mass spectrometer.

In the case of a TOF mass spectrometer, a certain acceleration voltage is applied, imparting an equally great kinetic energy to the ions. Then the time required by the respective ions to travel a certain drift distance through the flight tube is measured with a high degree of precision, because the velocity of the ions at the same kinetic energy depends on their mass.

The time-of-flight mass spectrometers have a very high scan rate and therefore achieve a very good resolution. They permit complete identification of the proteins and/or peptides present in the liquid sample.

This invention also relates to a device for qualitative and/or quantitative determination of a protein and/or peptide pattern in a liquid sample that is derived from the human or animal body.

This device includes a capillary electrophoresis device, an ionization unit, a mass spectrometer which is connected online via an interface and a computer unit having a program for controlling the device as well as for automatic analysis and storage of the measured values and for comparing the new measured values with the measured values already stored.

Such a device permits reliable determination of proteins and/or peptides in a complex matrix.

A capillary electrophoresis device therefore has a high separation efficiency, permitting determination of a complete protein and/or peptide pattern of the liquid sample, and it also has short analysis times, providing prompt information regarding the condition of the human or animal body from which the liquid sample was obtained.

For qualitative and/or quantitative determination of proteins and/or peptides, the capillary electrophoresis device is connected to a mass spectrometer which detects the proteins and/or peptides separated by capillary electrophoresis.

The computer unit contains a program for controlling the device. In addition, the measured values obtained by detection are automatically analyzed and stored. In addition, the program automatically compares the new measured values with the measured values already stored.

This comparison yields corresponding and deviating parameters, which can be used to describe the condition of the human or animal body.

In the case of determinations on multiple liquid samples derived from the same human or animal body in intervals in time, the program automatically determines, analyzes and stores the changes in the protein and/or peptide pattern.

This ensures the monitoring of the condition of a human or animal body over a longer period of time.

The program automatically creates a database consisting of reference values, sample values, deviations and correspondences which describe conditions and searches for the best possible correspondences in the case of new measurements. This makes it possible to have the conditions of human or animal bodies determined automatically.

According to a refinement of this invention, the program automatically determines the peptide or protein pattern of defined liquid samples and stores this data as normal values in a reference database.

This makes it possible to determine protein and/or peptide patterns of liquid samples of a human or animal body and store this information as reference data for which the condition is known. An extensive reference database is compiled and can be used automatically for comparison with new measurements.

An advantageous embodiment of the device according to this invention provides for the program to determine the peptide or protein pattern of undefined liquid samples automatically, to store this information as sample values in a separate database, to compare it with the normal values of the reference database and to automatically display and store deviations and/or correspondences.

Deviations or correspondences may be used as parameters for evaluating the condition of the human or animal body.

In addition, this provides for the liquid sample to be serum or urine.

These are liquid samples that are derived from the human body and having a protein and/or peptide composition which is especially suitable for providing information about the condition of the human or animal body.

According to a refinement of this invention, the proteins and peptides are cytokines, for example, in particular interleukins.

According to the information available today, these proteins are important proteins which control the functions of the human and animal body.

In addition, it is also possible for the mass spectrometer to be a time-of-flight mass spectrometer.

Time-of-flight mass spectrometers have a very high scan rate and therefore achieve a very good resolution. This makes it possible to determine the protein and/or peptide pattern completely.

In addition, a detector may also be arranged between the capillary electrophoresis device and the ionization unit. This is used in combination with mass spectrometry for better qualitative and quantitative determination of the protein and/or peptide pattern.

According to a refinement, the ionization unit has electrospray ionization.

Because of the relatively low energies acting on the molecules, electrospray ionization is a mild ionization technique, so that even sensitive molecules and to some extent even non-covalent aggregates can enter the mass analyzer without decomposing. This permits a very good identification of the proteins and/or peptides dissolved in the liquid sample.

This invention is explained in greater detail below on the basis of one embodiment, which is illustrated in the drawing, which shows:

FIG. 1 a schematic diagram of the method according to this invention.

FIG. 1 shows schematically the individual steps for qualitative and/or quantitative determination of a protein and/or peptide pattern in a liquid sample 10 that is derived from a human or animal body.

This shows the liquid sample 10, preferably serum or urine, the fractions 12 obtained after ultracentrifugation and ultrafiltration, a capillary electrophoresis device 14, an ionization unit 16 connected directly to the former, a mass spectrometer 20 connected online via an interface 18 and a computer unit 22 having a program for controlling the device and for automatic analysis and storage of the measured values and for comparison of new measured values with the measured-values already stored.

The liquid sample 10 that is derived from the human or animal body is first acidified with formic acid to a pH of 3. Then the liquid sample 10 is purified to remove unwanted particles by ultracentrifugation and is divided by ultrafiltration into fractions 12 which contain proteins and/or peptides of certain molecular sizes. Fractions 12 may be composed of proteins and/or peptides having a molecular weight of <3 kDa, 3-30 kDa, 30-50 kDa and >50 kDa.

Then the proteins and/or peptides of the individual fractions 12 are separated by capillary electrophoresis 14, ionized directly in an ionization unit 16 and transferred online to a mass spectrometer 20 connected thereto by an interface 18.

Of course, there is the possibility of using only fractions 12 whose proteins and/or peptides are needed for describing the condition of a human or animal body.

Mass spectrometer 20 is advantageously a TOF mass spectrometer, which has a very high scan rate, and yields a very good resolution.

The resulting mass spectrum may be used as a type of "fingerprint" to describe the overall condition of a human or animal body. In addition, however, it is also possible to identify the proteins individually and to draw conclusions regarding the condition of the human or animal body on the basis of the presence, absence and concentration of these proteins.

Computer unit 22 contains a program for controlling the device. In addition, the measured values obtained by detection may be analyzed automatically and stored in databases. In addition, this program automatically compares new measured values with the measured values already stored.

This comparison makes it possible to determine corresponding and deviating parameters which can be used to describe the condition of a human or animal body.

By means of the databases, it is possible to identify the same, similar or different conditions of the human or animal body.

The method according to this invention for qualitative and/or quantitative determination of a protein and/or peptide pattern in a liquid sample derived from a human or animal body can be carried out by technically trained personnel. Use of this method does not require a physician and it can also be used outside of medical laboratories.

The invention claimd is:

1. A method of qualitative or quantitative determination of a protein or peptide pattern of a liquid sample which has been derived from a human or animal body for monitoring a condition of the body, comprising the steps of:
   (a) establishing in a database a number of reference peptide patterns related to a condition of a human or animal body, said reference peptide patterns comprising at least a first peptide pattern and a second peptide pattern, the peptide patterns being defined by a list of signals comprising mass charge quotients;
   (b) separating the peptides or proteins of the liquid sample by capillary electrophoresis;
   (c) ionizing the peptides or proteins directly;
   (d) transferring the peptides or proteins to a mass spectrometer connected online via an interface for detection;
   (e) detecting qualitative or quantitative values of the protein or peptide pattern wherein more than 100 peptides or proteins are detected;
   (f) comparing the protein or peptide pattern detected with the reference peptide patterns in the database; and
   (g) automatically seeking for the protein or peptide pattern detected the reference peptide pattern in the database that most closely matches the detected protein or peptide pattern, wherein deviations or correspondences are used for evaluating the condition of the human or animal body.

2. The method according to claim 1, wherein serum or urine is used as the liquid sample.

3. The method according to claim 1, wherein qualitative or quantitative values are obtained for the protein or peptide pattern of the cytokines.

4. The method according to claim 1, wherein the liquid sample is first acidified, then purified to remove unwanted particles by ultracentrifugation or is divided into fractions containing proteins or peptides of certain molecular sizes, before being separated by capillary electrophoresis.

5. The method according to claim 4, wherein the fractions are composed of proteins or peptides of the molecular weights of <3 kDa, 3-30 kDa, 30-50 kDa and >50 kDa.

6. The method according to claim 1, wherein electrospray ionization is used for ionization of the proteins or peptides.

7. The method according to claim 1, wherein a time-of-flight mass spectrometer (TOF) is used as the mass spectrometer.

8. The method according to claim 1, wherein the proteins and peptides are interleukins.

9. A device for qualitative or quantitative determination of a protein or peptide pattern in a liquid sample derived from a human or animal body for monitoring a condition of the body, comprising:
   (a) a capillary electrophoresis device;
   (b) an ionization unit;
   (c) a mass spectrometer connected online via an interface; and
   (d) a computer unit having a program for controlling the device as well as for automatic analysis and storage in a database of a number of reference peptide patterns comprising at least a first peptide pattern and a second peptide pattern, the peptide patterns being defined by a list of signals comprising mass charge quotients, and for comparing a protein or peptide pattern detected with the reference peptide patterns in the database;

wherein said program automatically searches for a protein or peptide pattern that most closely matches the detected protein or peptide pattern, wherein deviations or correspondences are used for evaluating the condition of the human or animal body.

10. The device according to claim 9, wherein the database comprises a reference database and the program automatically determines the peptide or protein pattern of defined liquid samples and stores them as normal values in the reference database.

11. The device according to claim 10, wherein the program automatically determines the peptide or protein pattern of undefined liquid samples, stores them as sample values in the database, compares them with the normal values in the reference database and automatically displays deviations and/or correspondences with the reference peptide patterns.

12. The device according to claim 9, wherein the liquid sample is serum or urine.

13. The device according to claim 9, wherein the proteins and peptides are cytokines.

14. The device according to claim 13, wherein the proteins and peptides are interleukins.

15. The device according to claim 9, wherein the mass spectrometer is a flight-of-time mass spectrometer.

16. The device according to claim 9, wherein the ionization unit has electrospray ionization.

* * * * *